United States Patent [19]

Hutson

[11] 4,363,635
[45] Dec. 14, 1982

[54] METHOD AND APPARATUS FOR MEASURING BREATH ALCOHOL

[75] Inventor: Donald G. Hutson, El Cerrito, Calif.
[73] Assignee: Cal Detect, Inc., Richmond, Calif.
[21] Appl. No.: 228,119
[22] Filed: Jan. 26, 1981
[51] Int. Cl.³ .................. G01N 27/62; G01N 1/22
[52] U.S. Cl. .................. 436/132; 23/230 M; 23/232 R; 422/84; 422/93; 73/864.83; 250/343; 436/130
[58] Field of Search .............. 422/84, 85, 93; 137/625.44, 625.45; 128/719; 250/343, 344, 345; 324/71 SN, 71 R; 23/907, 232 E, 230 M, 232 R; 73/23, 864.83, 863.83

[56] References Cited

U.S. PATENT DOCUMENTS 3,830,630  8/1974  Kiefer et al. ............... 23/232 E
4,268,751  4/1979  Fritzlen et al. ............. 250/343
4,278,636  7/1981  Voigt et al. ................ 422/84

FOREIGN PATENT DOCUMENTS 816392  7/1969  Canada ..................... 73/864.83

Primary Examiner—Frank W. Lutter
Assistant Examiner—Chris Konkol
Attorney, Agent, or Firm—Polster, Polster and Lucchesi

[57] ABSTRACT

A method and apparatus for discriminating between alcohol and acetone in a breath sample and accurately measuring the alcohol level when acetone is present in the sample. The breath sample is measured with two different types of detectors and their outputs compared. One detector uses the principles of infrared (IR) absorption, the other detector is a semiconductor, commonly called a Taguci cell, or its equivalent. Automatic correction is provided for variations in sensitivity of the semiconductor.

10 Claims, 6 Drawing Figures

METHOD AND APPARATUS FOR MEASURING BREATH ALCOHOL

BACKGROUND OF THE INVENTION

The testing of a subject's breath to determine the amount of alcohol in the subject's blood, using an infrared detector that measures the absorption of infrared energy in the 3.3 to 3.48 micron energy region, is a well established technique, used by law enforcement and alcohol treatment centers. However, this method has a serious drawback in that the IR device can not distinguish between ethyl alcohol and acetone. Significant amounts of acetone appears in the breath of persons on stringent diets and in the breath of diabetics who are in ketosis, acidosis or diabetic coma. Courts have begun to take notice of this problem.

One of the objects of this invention is to provide apparatus and method for supplying a true measure of the alcohol content of breath containing a mixture of alcohol and acetone.

Other objects will become apparent to those skilled in the art in the light of the following description and accompanying drawing.

SUMMARY OF THE INVENTION

In accordance with this invention, generally stated, an analyzer for measuring the amount of alcohol in a breath sample is provided which includes an infrared (IR) detector, a semiconductor (SC) detector, means for exposing a portion of a given breath sample to the IR detector and a portion to the SC detector, means for comparing outputs from the IR detector and the SC detector and means for subtracting from the output of the IR detector an amount that is a function of the difference between the outputs of the IR and the SC detectors. The method includes establishing the output responses to an alcohol standard of an IR detector and a SC detector, measuring the output of the IR detector in response to its exposure to a portion of a breath sample, measuring the output from the SC detector in response to its exposure to a portion of the breath sample, comparing the outputs, and subtracting from the output of the IR detector an amount that is a function of the difference in output from the IR detector and that from the SC detector. In the preferred embodiment, the method includes applying a calibration factor to the output from the SC detector. In one embodiment the calibration factor is an average of a plurality of previous analyses. In the preferred embodiment of apparatus, not only are means provided for calibrating the SC detector, but means are provided for capturing a portion of the stream of breath sample as the IR detector is being exposed to it, and exposing the SC detector to the captured portion.

DESCRIPTION OF THE PREFERRED EMBODIMENT

Figure 1:
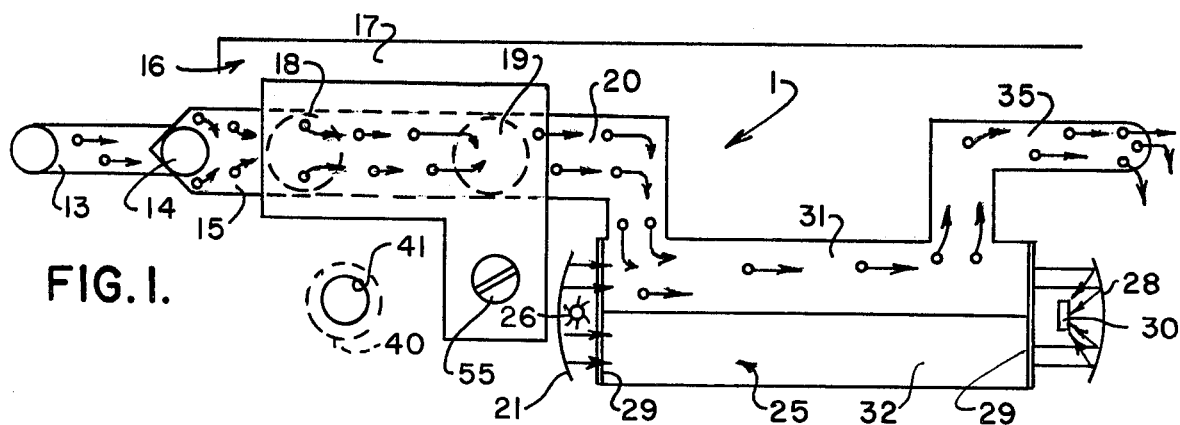
FIG. 1 is a somewhat diagrammatic view of one illustrative embodiment of apparatus of this invention.

Referring now to the drawing for one illustrative embodiment of apparatus of this invention, reference numeral 1 indicates the mechanical portion, and reference numeral 2, the electrical portion. Referring now to FIG. 1, an inlet breath line 13 communicates, through a check valve 14, with a passage 15 in a block 16, which in this embodiment is provided with a cover plate 7, with a flat upper surface 17. The passage 15 opens through the upper surface 17 in an inlet port 18. An outlet port 19 is the mouth of an outlet passage 20, which communicates with an infrared (IR) detector 25. The IR detector 25 can be of conventional design, with an IR source 26, mirrors 27 and 28, windows 29, an IR detector 30 with a filter to pass energy only in the range of 3.30 to 3.48 microns, a sample cell 31 and a reference cell 32. The sample cell is vented to the atmosphere through a passage 35.

Set into the block 16, in a socket 40, is a semiconductor cell or detector 43 of the type known as a Taguci cell. A restricted port 41 through the cover plate 7 opens through the surface 17 to the cell 43. A heater, not here shown, is provided to heat the cell to the temperature recommended by the manufacturer, generally in the neighborhood of 230° C.

An L-shaped arm 50 with a flat bottom surface 51 resting in slidable but substantially airtight contact with the upper surface 17 of the cover plate 7, is pivotally mounted on the block 16 by means of a pivot post 55. An elongated stem 52 of the arm 50 has a blind channel 53 extending lengthwise in it, interrupting the bottom surface 51 and, in the position of the arm shown in FIGS. 1, 2 and 3, serving as a passageway connecting the inlet port 18 with the outlet port 19. A foot portion 54 of the arm 50 is uninterrupted through its bottom surface, except for a bearing hole 56 through which the pivot post 55 extends. The bearing hole 56, perpendicular to the surface 17, is offset from the channel 53 so that there is no communication between the channel 53 and the hole 56.

Figures 2, 4:
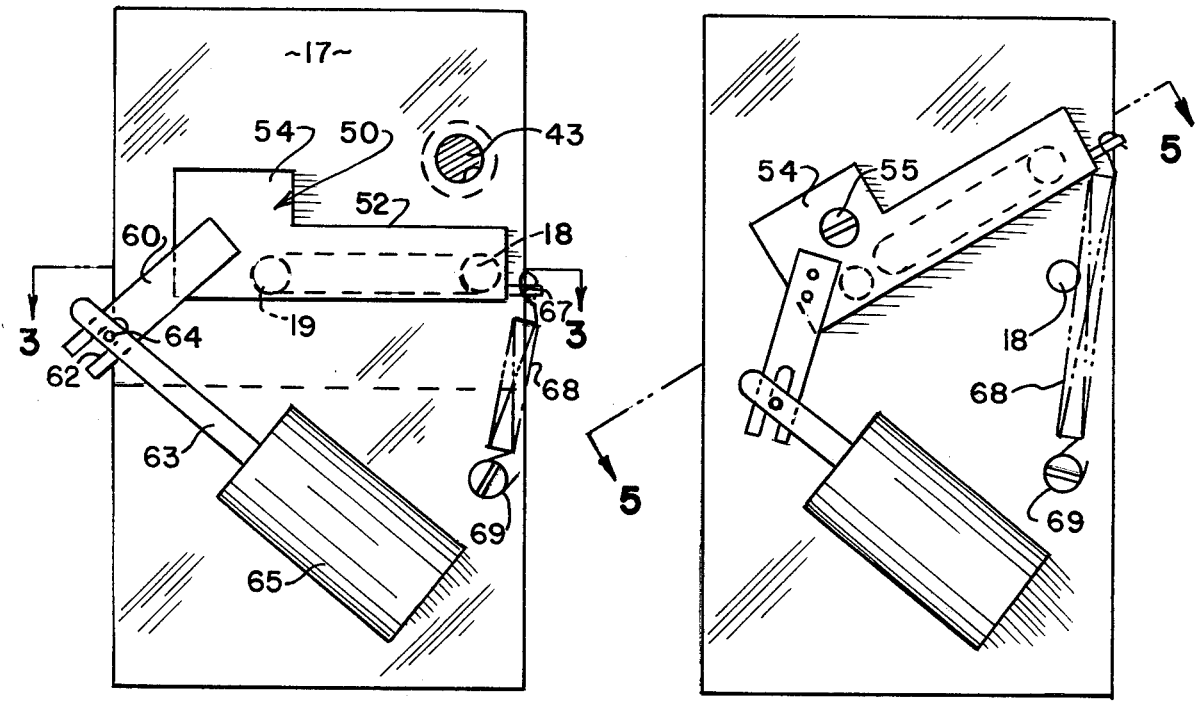
FIG. 2 is a top plan view of a portion of the sampling mechanism of the apparatus of FIG. 1.
FIG. 4 is a top plan view of the sampling apparatus of FIG. 2 in a second position.
Figure 3:
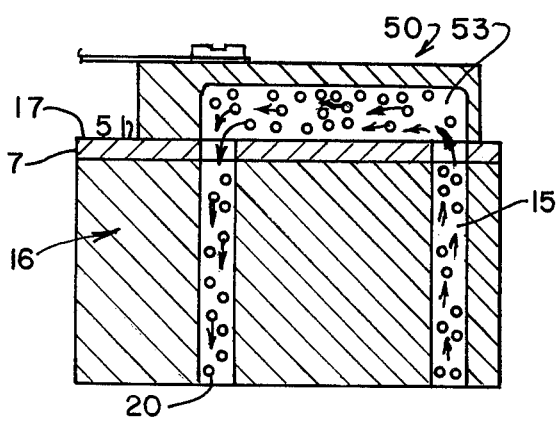
FIG. 3 is a sectional view taken along the line 3—3 of FIG. 2.

A bracket 60, secured to the arm 50, extends from and beyond the arm at an angle from the outside junction of the foot 54 and stem 52. The bracket 60 has at its outer end a yoke 62 in which a pin 64 of an actuating rod 63 extends and slides. The actuating rod 63 is reciprocated by a solenoid coil 65 mounted on the block 16. An eye 67 projects from the free end of the stem 52. On end of a helical spring 68 is hooked to the eye 67. The other end of the spring is hooked around a spring retaining pin 69 mounted in the block 16. In one position of the arm 50, the channel 53 communicates with and extends between the ports 18 and 19, as shown in FIGS. 2 and 3, and at another position, when the actuating rod 63 is retracted to rotate the arm about the pivot 55 against the bias of the spring 68, the channel communicates with the port 41, at which position, the inlet port 18 is open to the atmosphere, and the outlet port 19 is closed by the undersurface of the foot 54 of the arm, as shown particularly in FIGS. 4 and 5. In this way, the SC detector is not exposed to a moving stream of breath sample, which would otherwise tend to cool the surface of the sensor and produce inaccuracies in its output reading.

The trapped breath sample merely diffuses into the area around the cell 43.

Figure 6:
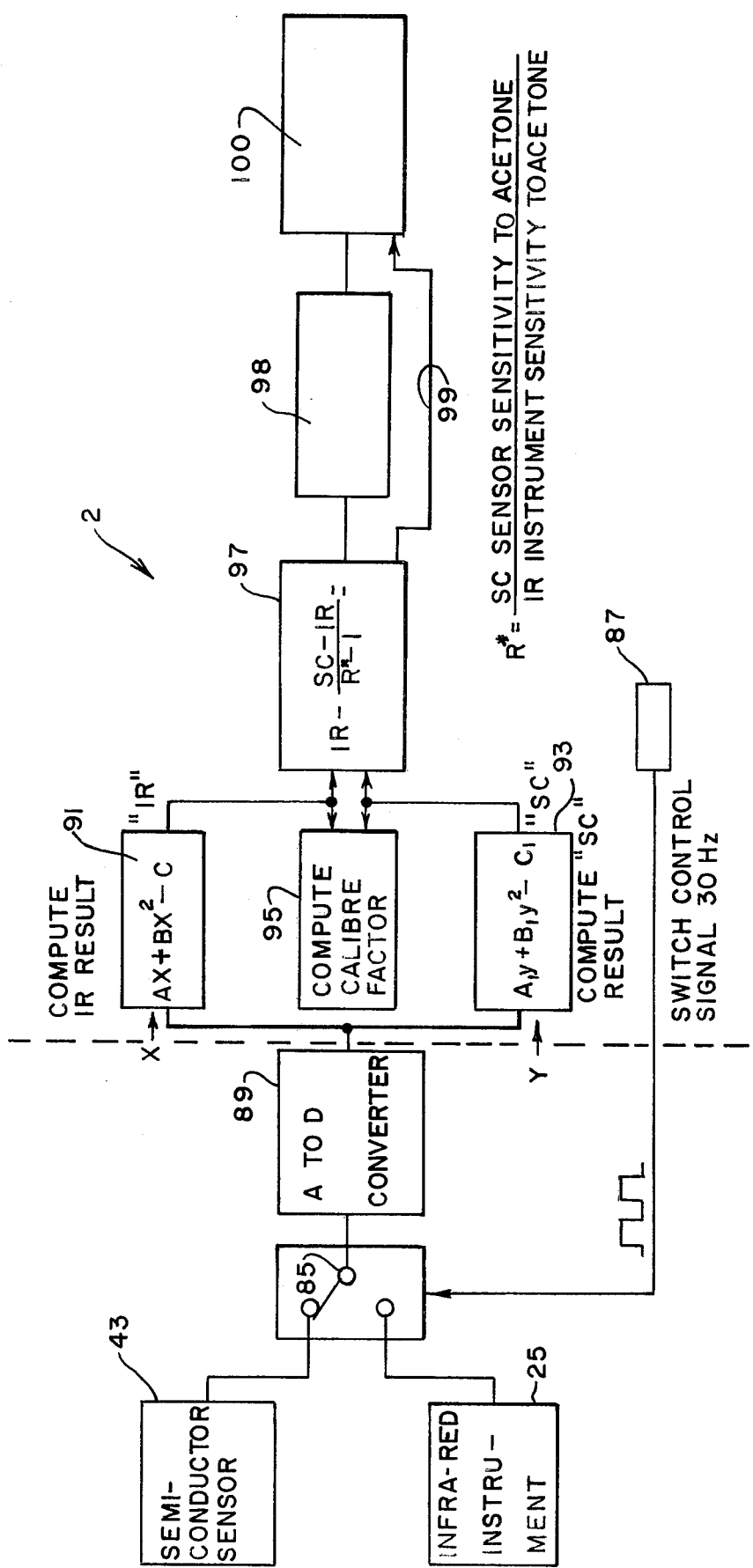
FIG. 6 is a schematic view of the electrical elements of the apparatus of this invention.

Referring now to FIG. 6, the infrared detector 25 and semiconductor detector 43 are electrically connected to an electronic switch 85 that is controlled by a signal from an appropriate generator 87. In the illustrative embodiment shown, the generator 87 produces a 30 hertz control signal, so that the switch connects the sensor 43 and instrument 25, alternately, 30 times a second to an analog-to-digital converter 89. The converter 89 is electrically connected in such a way as to feed the output (X) from the infrared instrument, in digital form, to an IR microprocessor 91, and to feed the output from the semiconductor sensor (Y) to an SC microprocessor 93. The two digital signals from the microprocessor computers 91 and 93 are fed to an analyzing microprocessor computer 97 to which the processors 91 and 93 are electrically connected and to a calibration factor microprocessor 95 electrically connected to the computer 97. A signal from the computer 97 represents the corrected IR reading, indicated in this schematic by the reference numeral 98, which is fed to a display 100, at which the results are displayed on a screen or printed, or both. An acetone reading level, indicated by reference numeral 99, is also fed to the display 100, in the embodiment shown, to be shown or printed separately. The display of the acetone level reading is not necessary, but is desirable, even in law enforcement application, because it is likely to lead to the immediate observation that the subject is in a diabetic coma, for example.

The method of this invention utilizes the fact that when the sensitivity of the IR detector and the SC detector to (ethyl) alcohol are made substantially identical, the sensitivity of the SC detector to acetone will be several times that of the IR detector. In carrying out the method of this invention, a subject is caused to blow into the inlet breath line 13, through the channel in the actuating arm, into the IR cell, the breath venting to atmosphere after passing through the cell. After a sufficient quantity of the subject's breath sample has passed through the IR cell to assure that deep lung air is being sampled, the electrical solenoid is energized to move the actuating arm to the position shown in FIGS. 4 and 5. There are a number of known ways of sensing the quantity of breath or the rate of increase of alcohol content in the breath sample, to ensure that alveolar air is being sampled, and the actuation of the solenoid can be made automatic.

Figure 5:
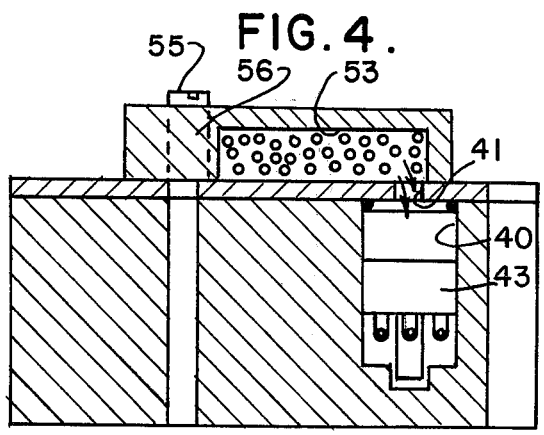
FIG. 5 is a sectional view taken along the line 5—5 of FIG. 4.

When the arm 50 is moved to the position shown in FIGS. 4 and 5, the channel 53 serves as a closed chamber, communicating only with the port 41, to permit the breath sample contained in the channel to diffuse into the cell 40 and around the SC element 43. This increases the surface conductivity of the SC element, allowing more current to flow across the element surface. This increase in current is converted to an electrical output, which increases as the amount of alcohol, or acetone, or both, increases. The relationship is nonlinear, but the signal is so processed as to make the voltage output proportional to the concentration of alcohol, or acetone, or both, present. Once the output signal has reached a maximum, the electrical solenoid is de-energized, allowing the arm to return to its original position, as shown in FIGS. 2 and 3.

This reconnects the breath inlet line to the IR cell and exposes the semiconductor cell to the atmosphere. The exposure of the cell to the atmosphere allows the alcohol and acetone to dissipate from the element surface, returning the surface conductivity to its original low value.

In FIGS. 1, 3 and 5, the breath sample is represented by small circles, and its movement, by arrows.

As has been indicated above, the signals (voltages) from the SC detector and the IR detector are fed alternately, through an electronic switch 85, to the converter 89. From the converter 89 the digital IR signal is processed by the processor 91 to a digital signal (number) representing the level of breath alcohol plus acetone in the original sample, in accordance with the formula $AX + BX^2 - C$, in which X is the digital signal from the IR detector and A, B and C are standard linearizing constants programmed into the microprocessor computer 91 for the particular IR instrument, as is well known in the art. Similarly, the signals from the SC sensor 43 are converted to digital form by the converter 89 and then processed by the processor 93 to a digital signal (number) representing the response of the SC detector to the level of breath alcohol plus acetone in the original sample, in accordance with the formula $A_1Y + B_1Y^2 - C_1$, wherein Y is the converted voltage from the SC detector, and $A_1$, $B_1$ and $C_1$ are linearizing constants programmed into the microprocessing computer 93 for the particular SC detector.

The two signals are further processed in the processor 97 by applying the following formula:

Corrected IR reading = $IR - (SC - IR)/(R - 1)$

Where R = (SC Acetone Sensitivity)/(IR Acetone Sensitivity). If the quantity $-(SC - IR)/(R - 1)$ is positive, the amount is set to zero, i.e., the raw IR reading is the correct one.

The ratio, R, is determined for a particular SC detector and IR detector by first exposing both sensors to a standard sample containing only alcohol, and adjusting the sensitivity so that both detectors read the true alcohol level. Both detectors are then exposed to a standard sample containing only acetone, and the SC reading is then divided by the IR reading. The ratio thus established will fall in the range of 2 to 7, depending primarily upon the filters used in the IR instrument. The center band pass normally falls at about 3.39 microns, but normal production tolerances may shift the center band pass to as low as 3.3 microns or as high as 3.48 microns. This will produce ratios that vary from 2 to 7, respectively.

As an example of the correction computation, assume that a simulated breath sample containing 0.02 gram % of acetone is analyzed and the output from the IR instrument produces a reading of 0.03 and the output from the SC detector produces a reading of 0.12, the ratio would be computed as 0.12/0.03, which equals 4.0. If both sensors are now exposed to a simulated breath sample containing 0.02 gram % of acetone and 0.10 gram % alcohol, the computed (raw) IR reading will be 0.13, i.e. 0.10+0.03, and the SC reading will be 0.22, i.e. 0.10+0.12.

The corrected IR reading will be 0.10, i.e., 0.13−(0.22−0.13)/(4−1), the true alcohol level.

This correction of the IR reading will be accurate as long as the sensitivity of both detectors remains constant. The IR instrument is inherently stable, but the SC detector sensitivity increases approximately 30% over a period of several weeks once a heater voltage has been applied. This gradual change in sensitivity is automatically corrected by comparing the computed IR result and the computed SC result. If the SC result differs from the IR result, a calibration factor, applied to the SC result, is altered slightly such that the next analysis will produce an SC result that more closely matches the IR result.

The comparison upon which the calibration factor is based, can be made as a result of the running of an external alcohol standard, or by an internal comparison at the running of each breath sample.

If an external alcohol standard is run before each test, as is the case in many law enforcement jurisdictions, the microprocessor program is designed to compute the calibration factor only when the alcohol standard is run, and the acetone concentration in breath samples run between standardizations has no effect upon the calibration factor.

If the comparison is to be made upon the running of each breath sample, the calibration factor, in the preferred embodiment of this invention, is made an average of the previous four analyses. When the instrument is first turned on, the semiconductor channel calibration factor will be adjusted automatically after four breath samples have been analyzed, and each time a sample is run, this calibration factor will be adjusted slightly to account for slow changes in the SC detector's sensitivity. If a breath sample containing acetone is analyzed, the contribution of the acetone to the IR result will be subtracted. This will alter the calibration factor slightly, and if a second analysis is done that also contains acetone, a small portion of the acetone contribution to the result will not be subtracted out. The calibration averaging technique has been selected so that a 0.07 gram % acetone sample will not affect the final IR result by more than 0.01 gram % when run two times in succession. In practice, acetone levels as high as 0.07 gram % would not be encountered in the driving population, and the chances of encountering any individual with such an acetone level in his breath are estimated to be less than 100,000 to 1.

It can be seen that because the amount of acetone is determined in each instance in order to obtain a corrected IR reading for alcohol, the amount of acetone can be displayed as well as the amount of alcohol. It is a simple matter to provide for the display of acetone to be different in time or place or both, or in form, e.g., printout versus screen, from that of the alcohol.

Numerous variations in the apparatus and method of this invention, within the scope of the appended claims, will occur to those skilled in the art in the light of the foregoing disclosure.

I claim:

1. A method of measuring the alcohol level of a breath sample containing alcohol and acetone, comprising calibrating an IR detector and an SC detector to establish their output responses to an alcohol standard; introducing to said IR detector a flowing stream of breath sample; measuring the output from said IR detector in response to its exposure to a portion of said breath sample; introducing to said SC detector a substantially static portion of said breath sample; measuring the output from said SC detector in response to its exposure to said portion of said breath sample; comparing said outputs, subtracting from the output from the IR detector an amount that is a function of the difference between the output from the IR detector and the output from the SC detector, and deriving an output signal from the said difference indicative of the amount of at least one of alcohol and acetone in said sample.

2. The method of claim 1 including applying a calibration factor to the output from the SC detector.

3. The method of claim 2 wherein the calibration factor is an average of a plurality of previous analyses.

4. The method of claim 2 wherein an external alcohol standard is run before each test, and the calibration factor is determined by said alcohol standard.

5. The method of claim 1 including reading out the acetone content of said breath sample as a function of the relative increase in output from the SC detector attributable to the presence of acetone.

6. The method of measuring the alcohol content of a breath sample containing alcohol and acetone comprising exposing to a stream of said sample an IR detector and to a substantially static portion of said sample an SC detector, comparing the outputs of said detectors, reducing the output from at least one of said detectors by an amount that is a function of the difference in output of said IR detector and said SC detector in response to the presence of acetone, and measuring said output signal.

7. In an analyzer for measuring the amount of alcohol in a breath sample, the improvement comprising an IR detector; an AC detector; means for exposing a flowing portion of said breath sample to said IR detector and a substantially static portion to said SC detector; means for comparing outputs from said IR detector and said SC detector, means for subtracting from the output of said IR detector an amount that is a function of the difference between the outputs of the IR and SC detectors, and means for deriving therefrom an output signal indicative of the amount of at least one of alcohol and acetone in said sample.

8. The analyzer of claim 7 wherein the breath sample is introduced in a stream and the means for exposing a portion of breath sample to the SC detector include means for capturing a portion of said stream as said IR detector is being exposed thereto, cutting off said stream, and substantially simultaneously exposing said SC detector to said captured substantially static portion.

9. The analyzer of claim 8 wherein the means for exposing a portion of breath sample to the SC detector comprises an open bottomed box-shaped arm mounted on a flat surface which, with the said arm, defines a hollow enclosure, said enclosure being selectively movable to a first position to communicate with a breath sample stream inlet and a breath sample stream outlet communicating with said IR detector, and to a second position to communicate with the SC detector, and means for moving said arm from said first position to said second position.

10. In an analyzer for measuring the amount of alcohol in a breath sample in a stream, the improvement comprising an IR detector; an SC detector; means for exposing a portion of said breath sample to said IR detector and means for exposing a portion of said sample to said SC detector, said means including means for capturing a portion of said stream as said IR detector is being exposed thereto for cutting off said stream, and substantially simultaneously exposing said SC detector to said captured portion, said means comprising an open bottomed box-shaped arm mounted on a flat surface which, with said arm, defines a hollow enclosure, said enclosure being selectively movable to a first position to communicate with a breath sample stream inlet and a breath sample stream outlet communicating with said IR detector, and to a second position to communicate with the SC detector, and means for moving said arm from said first position to said second position, said enclosure being elongated and said arm being pivotally mounted to said flat surface about an axis offset laterally from said enclosure, whereby, when said arm is moved around said axis from the first position to the second position, the enclosure communicates with neither the said inlet nor the said outlet.

* * * * *